(12) United States Patent
Wasserscheid et al.

(10) Patent No.: US 7,544,807 B2
(45) Date of Patent: *Jun. 9, 2009

(54) IONIC LIQUIDS

(75) Inventors: Peter Wasserscheid, Erlangen (DE); Andreas Bösmann, Heβdorf (DE); Roy Van Hal, Köln (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/833,529

(22) Filed: Aug. 3, 2007

(65) Prior Publication Data

US 2008/0033178 A1 Feb. 7, 2008

Related U.S. Application Data

(63) Continuation-in-part of application No. 10/798,796, filed on Mar. 11, 2004, now Pat. No. 7,252,791, which is a continuation-in-part of application No. PCT/EP02/10206, filed on Sep. 11, 2002.

(30) Foreign Application Priority Data

Sep. 17, 2001 (DE) .................. 101 45 747

(51) Int. Cl.
*C07D 401/04* (2006.01)
*C07D 213/26* (2006.01)
*C07D 233/00* (2006.01)
*C07F 9/02* (2006.01)
*C07D 229/00* (2006.01)

(52) U.S. Cl. .............. 546/274.1; 546/347; 568/9; 548/951; 548/335.1

(58) Field of Classification Search .......... 546/274.1, 546/347; 568/9; 548/951, 335.1
See application file for complete search history.

(56) References Cited

U.S. PATENT DOCUMENTS

| | | | | |
|---|---|---|---|---|
| 3,471,544 A | * | 10/1969 | Tomalia ............. | 558/22 |
| 5,994,602 A | | 11/1999 | Abdul-Sada et al. | |
| 6,245,918 B1 | | 6/2001 | Olivier | |
| 7,252,791 B2 | * | 8/2007 | Wasserscheid et al. ..... | 252/364 |
| 2006/0063945 A1 | * | 3/2006 | Wasserscheid et al. ........ | 554/85 |

FOREIGN PATENT DOCUMENTS

| | | |
|---|---|---|
| EP | 1182196 A | 2/2002 |
| EP | 1182197 A | 2/2002 |
| EP | 1182196 B1 | 6/2004 |
| GB | 1050791 A | 12/1966 |
| GB | 1440238 A | 6/1976 |
| WO | 99/40025 A | 8/1999 |
| WO | WO00/16902 | 3/2000 |

OTHER PUBLICATIONS

Hcaplus abstract 71:23179a, 23192a.*
Kloubek, J. et al., "Alkyl Esters of Sulfuric Acid and their Salts", Chemical Abstracts, Apr. 12, 1965, vol. 62, No. 8, Abstract No. 9012a, Columbus, Ohio, US.
Corkill, et. al., Database accession No. 4171557, XP002224892 abstract; Database Crossfire Beilstein Online!, 1966, vol. 62, p. 987, Frankfurt Main, DE.
Yu, Z.-J. et. al., Database accession No. 3643077, XP002224893 abstract; Database Crossfire Beilstein Online!, 1990, vol. 94, No. 9, pp. 3675-3681. Frankfurt Main, DE.
Packter, A. et. al., Database accession No. 6709453, 6709293, 6709083, 6708828, 6708655, XP002224894 abstract; Database Crossfire Beilstein Online!, 1963, vol. 15, pp. 317-324.
Meguro, K. et. al., Database accession No. 3643865, XP002224895 abstract, Database Crossfire Beilstein Online!, 1959, vol. 80, p. 818.
Tomasic, V. et. al., Database accession No. 7847922, XP002224896 abstract, Database Crossfire Beilstein Online!, 1997, vol. 101, No. 12, pp. 1942-1948.
Jokela, P. et. al., Database accession No. 6465924, XP002224896 abstract, Database Crossfire Beilstein Online!, 1987, vol. 91, No. 12, pp. 3291-3298.
Cuccovia, I.M. et. al., Database accession No. 3814288, XP002224898 abstract, Database Crossfire Beilstein Online!, 2000, vol. 2, No. 9, pp. 1896-1907.
Bolle, B., Database accession No. 3862916, 3823539, 3821574, 3808539, XP002224899, Database Crossfire Beilstein Online!, 1953, vol. 38, p. 159.
Abramzon, A.A. et. al., Database accession No. 8461725, XP002224900 abstract, Database Crossfire Beilstein Online!, 1999, vol. 72, No. 4, pp. 666-669.
Bonilha, B.S. et. al., Database accession No. 3800408, XP002224901, Database Crossfire Beilstein Online!, 1989, vol. 93, No. 1, pp. 367-372.

(Continued)

*Primary Examiner*—Janet L Andres
*Assistant Examiner*—Binta M Robinson
(74) *Attorney, Agent, or Firm*—Rick Matos; Innovar, L.L.C.

(57) ABSTRACT

Low melting ionic compounds of the general formula (cation) (R'SO$_4$) in which R' is a branched or linear, saturated or unsaturated, aliphatic or alicyclic functionalized or non-functionalized hydrocarbon chain with 3-36 carbon atoms are provided. These compounds can serve as ionic liquids, e.g. as solvents or solvent additives in chemical reactions, as extraction agents or as heat carriers. The compounds comprise a cation and anionic sulfate ester.

12 Claims, No Drawings

OTHER PUBLICATIONS

Patent Abstracts of Japan, vol. 017, 594, Oct. 29, 1993, JP 05 0178798 A; Kao Corp., Jul. 20, 1993 abstract.

Guilloteau-Bertin, B. et. al., Stereocontrolled Alkylation of Chiral Pyridinium Salt Toward a Short Enantioselective Access to 2-Alkyl- and 2, 6-Dialkyl-1, 2, 5, 6- Tetrahydropyridines, Eur. J. Org. Chem., 2000, No. 8, XP002224904, pp. 1391-1399.

Thomas Welton, "Room Temperature Ionic Liquids. Solvents for Synthesis and Catalysis", Chem. Rev. (1999), vol. 99, pp. 2071-2083.

Peter Wasserscheid, Wilhelm Keim, "Ionic Liquids- New 'Solutions' for Transition Metal Catalysis", Angew. Chem. Int. Ed. (2000), vol. 39, pp. 3772-3789.

Kang et. al., "Improvement of the Phase-Transfer Catalysis Method for Synthesis of Glycidyl Ether", Journal of the American Oil Chemist' Society (2000), 78 (4), pp. 423-429.

High Pressure Phase Behavior of Ionic Liquid/CO2 Systems; Lynnette A. Blanchard et al. ;American Chemical Society; published on web Mar. 7, 2001; 10.1021/jp003309d.

* cited by examiner

IONIC LIQUIDS

CROSS REFERENCE TO EARLIER FILED APPLICATIONS

The present application is a CONTINUATION-IN-PART of U.S. application Ser. No. 10/798,796 filed Mar. 11, 2004, which is a CONTINUATION-IN-PART of PCT International Application Ser. No. PCT/EP02/10206 filed Sep. 11, 2002 and published as PCT International Publication No. WO 03/022812 on Mar. 20, 2003, which claims the benefit of priority of German Patent Application Ser. No. DE 2001-10145747.2 filed Sep. 17, 2001, the entire disclosures of which are hereby incorporated by reference.

FIELD OF THE INVENTION

The present invention relates to ionic liquids with the general formula (cation) (R'SO$_4$), wherein R' is a branched or linear, saturated or unsaturated, aliphatic or alicyclic, functionalized or non-functionalized hydrocarbon chain with 3-36 carbon atoms. These novel ionic liquids can be used e.g. as solvents or solvent additives in chemical reactions, as extraction agents or as heat carriers.

BACKGROUND OF THE INVENTION

The term ionic liquids should be understood to mean salts or mixtures of salts whose melting point is below 100° C. (P. Wasserscheid, W. Keim, *Angew. Chem.* 2001, 112, 3926). Salts of this type known from the literature consists of anions, such as halogenostannates, halogenoaluminates, hexafluorophosphates or tetrafluoroborates combined with substituted ammonium cations, phosphonium cations, pyridinum cations or imidazolium cations to thereby form salts. Several publications have already described the use of ionic liquids as solvents for chemical reactions (T. Welton, Chem. Rev. 1999, 99, 2071, P. Wasserscheid, W. Keim, *Angew. Chem.*, 2000, 112, 3926). For example, hydrogenation reactions of olefins with rhodium(I) (P. A. Z. Suarez, J. E. L. Dullius, S. Einloft, R. F. de Souza and J. Dupont, *Polyhedron* 15/7, 1996, 1217-1219), ruthenium(II) and cobalt(II) complexes (P. A. Z. Suarez, J. E. L. Dullius, S. Einloft, R. F. de Souza and J. Dupont, *Inorganica Chimica Acta* 255, 1997, 207-209) have been carried out successfully in ionic liquids with tetrafluoroborate anion. The hydroformylation of functionalized and non-functionalized olefins is possible with rhodium catalysts in ionic liquids with weakly coordinating anions (e.g. PF$_6^-$, BF$_4^-$) (Y. Chauvin, L. Mussmann, H. Olivier, European Patent, EP 776880, 1997; Y. Chauvin, L. Mussmann, H. Olivier, *Angew. Chem., Int. Ed. Engl.*, 1995, 34, 2698; W. Keim, D. Vogt, H. Waffenschmidt, P. Wasserscheid, *J. of Cat.*, 1999, 186, 481).

Further important fields of application of ionic liquids consists of their use as extraction agents for material separation (J. G. Huddleston, H. D. Willauer, R. P. Swatloski, A. E. Visser, R. D. Rogers, *Chem. Commun.* 1998, 1765-1766; b) A. E. Visser, R. P. Swatlowski, R. D. Rogers, *Green Chemistry* 2000, 2(1), 1-4) and of their use as heat carrier (M. L. Mutch, J. S. Wilkes, *Proceedings of the Eleventh International Symposium on Molten Salts*, P. C. Trulove, H. C. De Long, G. R. Stafford and S. Deki (Hrsg.), Proceedings Volume 98-11, The Electrochemical Society, Inc, Pennington, N.J.; 1998, page 254).

Even if the definition of an ionic liquid includes those salts whose melting point is between the room temperature and 100° C. it is still necessary and desirable for many applications for the ionic liquids to be liquid at temperatures below room temperature.

Numerous examples of such ionic liquids are known; however, as a rule these systems possess halide ions such as F$^-$, Cl$^-$, Br$^-$ or I$^-$ or those anions that contain halogen atoms. Typical representatives of the latter anions are—without any claim to completeness—(BF$_4$)$^-$, (PF$_6$)$^-$, (CF$_3$COO)$^-$, (CF$_3$SO$_3$)$^-$, ((CF$_3$SO$_2$)$_2$N)$^-$, (AlCl$_4$)$^-$, (Al$_2$Cl$_7$)$^-$ or (SnCl$_3$)$^-$. The use of such anions containing halogen atoms imposes serious restrictions on the applicability of the corresponding ionic liquids: a) the use of these anions leads to considerable costs since even the alkali salts of these ions are very expensive; b) the hydrolysis products of these anions containing halogen atoms lead to considerable corrosion in steel reactors and in some instances also in glass reactors; and c) the thermal disposal of a "spent" ionic liquid with anions containing halogen atoms usually causes corrosion and environmental problems and is therefore very costly. The disposal via degradation in a biological clarification plant is also rendered difficult by the presence of anions containing halogen atoms.

In general, ionic liquids free from halogen atoms are therefore of particular interest since they possess the following properties:

a) a melting point and/or glass transition point of less than 25° C.;

b) hydrolytic-stability in neutral aqueous solution (pH=7) up to 80° C.;

c) disposal of by thermal means without the formation of problematic combustion gases;

d) degradability in biological clarification plants; and e) commercially available of the anion as an alkali salt at a favorable price.

Among the ionic liquids free from halogen atoms according to the state of the art, there have been no representatives so far capable of satisfying this complex technical requirement profile. Thus nitrate melts, nitrite melts, sulfate melts (J. S. Wilkes, M. J. Zaworotko, J. Chem. *Soc. Chem. Commun.* 1992, 965) and benzene sulfonate melts (H. Waffenschmidt, Dissertation, RWTH Aachen 2000) are known, however, these ionic liquids have melting points above room temperature. Hydrogen sulfates and hydrogen phosphates react in aqueous solution while splitting off one or several protons and form acidic aqueous solutions. Methyl sulfate and ethyl sulfate melts exhibit a distinct hydrolysis after only 1 h at 80° C. in aqueous solution with the formation of hydrogen sulfate anions and the corresponding alcohol (compare also comparative examples 1 and 2).

Therefore, a need remains for ionic liquids that have a low melting point and possess other advantageous properties as described herein.

SUMMARY OF THE INVENTION

Ionic liquids consisting of a combination of a suitable organic cation, e.g. imidazolium cation, pyridinium cation, phosphonium cation or ammonium cation, being particularly suitable examples, and an anion, having the general formula (R'SO$_4$), wherein R' is a linear or branched, saturated or unsaturated, aliphatic or alicyclic, functionalized or non-functionalized alkyl radical with 3-36 carbon atoms, possesses some or all of the above-mentioned advantageous properties. The ionic liquids according to the invention possess, on the one hand, a melting point and/or glass transition point of less than 25° C. They are also stable to hydrolysis in neutral aqueous solution (pH=7) up to 80° C. The ionic liquids according to this invention cause only form CO$_2$, H$_2$O and $SO_2$ during combustion. A further essential advantage of the novel ionic liquids according to the invention is the fact that many alkali salts with the general formula (alkalinisation) (R'—$SO_4$), wherein R' is a linear or branched, functionalized or non-functionalized, saturated or unsaturated, aliphatic or alicyclic alkyl radical with 3-36 carbon atoms, are readily available raw materials in the detergents, cosmetics and cleaning agents industries. This has lead to an extraordinarily high level of knowledge on the toxicological properties and the biological degradation behavior of the anion component (R'$SO_4$). From this, the conclusion can be drawn that the disposal of the ionic liquids according to the invention "spent" in technical applications can be carried out without problems in biological clarification plants.

DETAILED DESCRIPTION OF THE INVENTION

The present invention provides ionic liquids possessing a combination of most or all of the above-mentioned properties, thereby rendering them as ideal solvents and/or solvent additives for stoichiometric or catalytic chemical reactions and for their use as extraction agents and as heat carriers.

The invention provides an ionic liquid of the Formula 1

(cation)(R'$SO_4$)      Formula 1 wherein:

the cation is selected from the group consisting of:

1) quaternary ammonium cation with the general formula $(NR_1R_2R_3R)^+$;

2) phosphonium cation with the general formula $(PR_1R_2R_3R)^+$;

3) imidazolium cation with the general formula

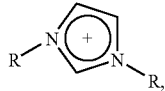

in which the imidazole core may be substituted with at least one group selected from $C_1$-$C_6$ alkyl groups, $C_1$-$C_6$ alkoxy groups, $C_1$-$C_6$ hydroxyalkyl groups, $C_1$-$C_6$ aminoalkyl groups, $C_5$-$C_{12}$ aryl groups or $C_5$-$C_{12}$-aryl-$C_1$-$C_6$ alkyl groups;

4) pyridinium cation with the general formula

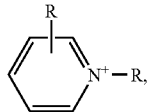

in which the pyridine core may be substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group;

5) pyrazolium cation with the general formula

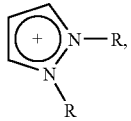

in which the pyrazole core may be substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group; and 6) triazolium cation with the general formula

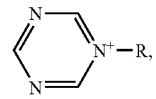

in which the triazole core may be substituted with at least one group selected from $C_1$-$C_6$ alkyl groups, $C_1$-$C_6$ alkoxy groups, $C_1$-$C_6$ hydroxyalkyl groups, $C_1$-$C_6$ aminoalkyl groups, $C_5$-$C_{12}$ aryl groups or $C_5$-$C_{12}$-aryl-$C_1$-$C_6$ alkyl group;

wherein and the radicals $R^1$, $R^2$, $R^3$ are selected independently of each other from the group consisting of:

hydrogen;

linear or branched, saturated or unsaturated, aliphatic or alicyclic alkyl groups with 1 to 20 carbon atoms;

heteroaryl groups, heteroaryl-$C_1$-$C_6$ alkyl groups with 3 to 8 carbon atoms in the heteroaryl radical and at least one heteroatom selected from N, O and S which may be substituted with at least one group selected from $C_1$-$C_6$ alkyl groups and/or halogen atoms;

aryl, aryl-$C_1$-$C_6$ alkyl groups with 5 to 12 carbon atoms in the aryl radical, which may optionally be substituted with at least one $C_1$-$C_6$ alkyl group and/or a halogen atom; and the radical R is selected from the group consisting of:

linear or branched, saturated or unsaturated, aliphatic or alicyclic alkyl groups with 1 to 20 carbon atoms;

heteroaryl-$C_1$-$C_6$ alkyl groups with 3 to 8 carbon atoms in the aryl radical and at least one heteroatom selected from N, O and S, which may be substituted with at least one $C_1$-$C_6$ alkyl group and/or halogen atom;

aryl-$C_1$-$C_6$ alkyl groups with 5 to 12 carbon atoms in the aryl radical, which may be substituted with at least one $C_1$-$C_6$ alkyl group and/or halogen atom; and R' is selected from the group consisting of a linear or branched, saturated or unsaturated, aliphatic or alicyclic, functionalized or non-functionalized alkyl radical with 3-36 carbon atoms, wherein R' is optionally functionalized with one or more X groups, wherein X is selected from the group consisting of an —OH, —OR", —COOH, —COOR", —$NH_2$, —$SO_4$, —F, —Cl, —Br, —I or —CN, wherein R" is selected from the group consisting of a branched or linear hydrocarbon chain with 1-12 carbon atoms; excluding N-methylpyridinium dodecyl sulfate and N-phenylethylpyridinium dodecyl sulfate.

In specific embodiments, the cation of the invention is a nitrogen-containing cation selected from the group consisting of a quaternary ammonium cation, an imidazolium cation, a pyridinium cation, a pyrazolium cation, and a triazolium cation. In even more specific embodiments, each cation is as defined herein.

Ionic liquids that contain mixtures of different ionic liquids with the general Formula 1 can also be produced and used according to the invention. Likewise, ionic liquid mixtures comprising different anions but the same cations are be produced and used according to the invention. The invention also contemplates preparation and use of ionic liquid mixtures comprising different cations but the same anions. These systems can be easily obtained from the mixtures of the corresponding alkali salts and from other corresponding starting materials that are available in industry.

The cations of the invention are readily available in free base form or in salt form from commercial suppliers. Likewise, the anions, the sulfate esters, of the invention are available in free acid or in salt form from commercial suppliers.

Some specific embodiments of the invention include those wherein: 1) the anion has an empirical formula selected from the group consisting of $C_4H_9SO_4$, $C_8H_{17}SO_4$ or $C_{12}H_{25}SO_4$; 2) the ionic liquid has a melting point of less than 75 C; 3) the ionic liquid has a melting point of less than 50 C; 4) the sulfate ester is an alkyl sulfate ester, wherein the alkyl moiety is selected from the group consisting of butyl, octyl, 2-ethylhexyl, and dodecyl; 5) the ionic liquid is used as a phase transfer catalyst; 6) the cation is a nitrogen containing cation selected from the group consisting of 1-ethyl-3-methylimidazolium, 1-butyl-3-methylimidazolium butyl, 1-hexyl-3-methylimidazolium, 1-octyl-3-methylimidazolium, 1-decyl-3-methylimidazolium, 1-dodecyl-3-methylimidazolium, 1-butyl-pyridinium, trimethyldecylammonium, trioctylmethylammonium, trimethyldecylammonium, and trihexyltetradecylphosphonium; 7) the ionic liquid is used as a solvent; 8) the ionic liquid is used as a solvent additive; 9) the ionic liquid is used as an extraction solvent; 10) the ionic liquid is used as a heat carrier or heat carrier additive; 11) the compound of the Formula 1 is used in a reaction catalyzed by a transition metal; 12) the compound of the Formula 1 is used in a hydroformylation reaction, oligomerization reaction, esterification reaction, isomerization reaction or amide bond-forming reaction; 13) the compound of the Formula 1 is used in a reaction catalyzed by an enzyme or biocatalyst; 14). the compound of the Formula 1 is used in an oligomerization reaction, C—C bond-forming reaction, esterification reaction, isomerization reaction, or amide bond-forming reaction; 15) the ionic liquid has a melting point of less than 25 C.; and/or 16) the compound of the Formula 1 is substantially hydrolytically stable in neutral aqueous solution (pH=7) up to 80° C.

According to one aspect of the invention, the compound of the Formula 1 is used as a phase transfer catalyst. In this case, a chemical reaction is conducted in a biphasic or multiphasic system which is a solvent-solvent system or a solvent-solid system. In a biphasic solvent-solvent system, the solvents are substantially immiscible solvents such that two or more separate phases are formed. The compound of the Formula 1 is then able to enter at least two of the phases to serve as a phase transfer catalyst.

The compound of the Formula 1 can be used in almost any reaction wherein a salt can aid in the reaction or improve reaction conditions. For example, the compound of the Formula 1 can be used in a hydroformylation reaction, oligomerization reaction, esterification reaction, isomerization reaction, C—C bond-forming reaction, or amide bond-forming reaction. The compound of the Formula 1 can be used in a transition metal catalyzed, enzyme catalyzed or biocatalyst catalyzed chemical reaction. For example, an enzyme catalyzed esterification reaction is conducted in the presence of the reactants, enzyme, solvent and the compound of the Formula 1, whereby the compound of the Formula 1 improves the results obtained with the enzyme catalyzed reaction.

According to another aspect of the invention, the compound of the Formula 1 is used as a solvent. In this case, one or more other compounds are dissolved with the compound of the Formula 1 in the liquid state. Depending upon the melting point of the compound of the Formula 1 used, heat may have to be employed to render it a liquid.

Another aspect of the invention provides the compound of the Formula 1 as a solvent additive. In this case, the compound of the Formula 1 is added to a solvent or mixture of solvents, wherein its desired properties or functionalities are exploited. As a solvent additive, the compound of the Formula 1 can alter the properties of the solvent to form a more advantageous mixture.

In the liquid form, the compound of the Formula 1 can serve as an extraction solvent, whereby one or more compounds are extracted from a solid, semisolid or liquid. In this case, the solid, semisolid or liquid is exposed to the compound of the Formula 1 for a sufficient period of time and at a temperature sufficient to extract the desired compound(s) from the solid, semisolid or liquid. The compound of the Formula 1 will generally be substantially immiscible with the other liquid from which the desired extract will be obtained. Heat may be employed to dissolve the compound of the Formula 1.

Since it is a low melting material and it does not corrode metal or synthetic conduits significantly, the compound of the Formula 1 can serve as a heat carrier liquid when it is melted. In this case, the molten compound of the Formula 1 can conduct heat from one area of a heat exchange unit to another area. For example, a heat exchange unit is operably attached to a vessel. The heat exchange unit containing the compound of the Formula 1 heats the compound that is then conducted via conduit to a jacket surrounding or within the vessel. The vessel removes some of the heat from the liquid, which then returns to the heat exchange unit for reheating. By way of this recirculation, the compound of the Formula 1 conducts heat from the heat exchanger to the vessel. In a similar fashion, the compound of the Formula 1 can be recirculated to remove heat from the vessel. When used as a heat carrier additive, the compound of the Formula 1 alters/improves the properties/performance of a first heat carrier.

The following ionic liquids according to the invention and their mixtures of two or more different ones are particularly suitable:

1-ethyl-3-methylimidazolium butyl sulfate
1-ethyl-3-methylimidazolium octyl sulfate
1-ethyl-3-methylimidazolium 2-ethylhexyl sulfate
1-ethyl-3-methylimidazolium dodecyl sulfate
1-butyl-3-methylimidazolium butyl sulfate
1-butyl-3-methylimidazolium octyl sulfate
1-butyl-3-methylimidazolium 2-ethylhexyl sulfate
1-butyl-3-methylimidazolium dodecyl sulfate
1-hexyl-3-methylimidazolium butyl sulfate
1-hexyl-3-methylimidazolium octyl sulfate
1-hexyl-3-methylimidazolium 2-ethylhexyl sulfate
1-hexyl-3-methylimidazolium dodecyl sulfate
1-octyl-3-methylimidazolium butyl sulfate
1-octyl-3-methylimidazolium octyl sulfate
1-octyl-3-methylimidazolium 2-ethylhexyl sulfate
1-octyl-3-methylimidazolium dodecyl sulfate
1-decyl-3-methylimidazolium butyl sulfate
1-decyl-3-methylimidazolium octyl sulfate
1-decyl-3-methylimidazolium 2-ethylhexyl sulfate
1-decyl-3-methylimidazolium dodecyl sulfate
1-dodecyl-3-methylimidazolium butyl sulfate
1-dodecyl-3-methylimidazolium octyl sulfate
1-dodecyl-3-methylimidazolium 2-ethylhexyl sulfate
1-dodecyl-3-methylimidazolium dodecyl sulfate
1-dodecyl-3-methylimidazolium tetrafluoroborate
1-butyl-pyridinium butyl sulfate
1-butyl-pyridinium octyl sulfate
1-butyl-pyridinium 2-ethylhexyl sulfate
1-butyl-pyridinium dodecyl sulfate
trimethyldecylammonium butyl sulfate
trimethyldecylammonium octyl sulfate
trimethyldecylammonium 2-ethylhexyl sulfate trimethyldecylammonium dodecyl sulfate
trioctylmethylammonium butyl sulfate
trioctylmethylammonium octyl sulfate
trioctylmethylammonium 2-ethylhexyl sulfate
trioctylmethylammonium dodecyl sulfate
trimethyldecylammonium butyl sulfate
trimethyldecylammonium octyl sulfate
trihexyltetradecylphosphonium butyl sulfate
trihexyltetradecylphosphonium octyl sulfate
trihexyltetradecylphosphonium 2-ethylhexyl sulfate
trihexyltetradecylphosphonium dodecyl sulfate
1,3-dialkyl-(2- or 4-hydroxyalkyl)imidazolium alkyl sulfate
1-alkyl-(2-, 3-, or 4-hydroxyalkyl)pyridinium alkyl sulfate
1,2-dialkyl-(3- or 4-hydroxyalkyl)pyrazolium alkyl sulfate
1-alkyl-(2- or 4-hydroxyalkyl)triazolium alkyl sulfate.

The above-mentioned ionic liquids are prepared according to the procedures described in the following examples. In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration.

The following examples should not be considered exhaustive, but merely illustrative of only a few of the many embodiments contemplated by the present invention.

EXAMPLE 1

1,3-Dimethylimidazolium octyl sulfate ((MMIM)(OCSO$_4$))

Preparation:

To a solution of 47.18 g (355.8 mmole) of 1,3-dimethylimidazolium chloride ((MMIM) Cl) in 400 ml of methylene chloride rendered absolute, 95.00 g (minimum 355.8 mmole) of sodium octyl sulfate (technical grade; content ≧87%) are added in small portions. The batch is stirred for 40 hours under blanketing gas. The solid is filtered off and washed with methylene chloride. The organic phase is concentrated and dried under a high vacuum to give 87.55 g (MMIM) (OCSO$_4$) (285.7 mmole; 80% of the theoretical yield) in the form of a yellowish liquid.

$^1$H-NMR (300 MHz, d$^6$-DMSO): δ=8.87 (s, 1H, N—CH—N), 7.45, 7.44 (one s in each case, 1H in each case, N—CH), 3.87 (mult., 8H, N—CH$_3$, S—O—CH$_2$—), 1.57 (mult., 2H, S—O—CH$_2$—CH$_2$—), 1.29 (k, B, 10H, S—O—CH$_2$—CH$_2$—(CH$_2$)$_5$—), 0.89 (t, J=6.6 Hz, 3H, —CH$_2$—CH$_3$) ppm, $^{13}$C-NMR (75 MHz, d 6-DMSO): δ=136.7, 122.8, 116.8, 35.1, 30.9, 28.7, 28.4, 25.1, 21.7, 12.8 ppm, Viscosity: The product exhibits a structural viscosity. The viscosity is strongly dependent on the conditions of measurement.

EXAMPLE 2

1-n-Butyl-3-methylimidazolium octyl sulfate ((BMIM) (OCSO$_4$))

Preparation:

84.55 g (0.484 mole) of 1-butyl-3-methylimidazolium chloride (BMIM Cl) and 101.1 g (minimum 0.379 mole) of sodium octyl sulfate (technical grade; content ≧87%) are dissolved in 200 ml of hot water. The water is slowly removed under vacuum. The solid formed is filtered off after dissolving the batch in methylene chloride. The filtrate is washed until the aqueous phase is colourless and free from chloride. The organic phase is dried over Na$_2$SO$_4$. Concentrating and drying under a high vacuum gives 111.0 g (0.319 mmole; 73% of the theoretical yield, based on sodium octyl sulfate) of an oily yellow liquid.

1H-NMR (300 MHz, d $^6$-DMSO): δ=9.16 (s, 1H, N—CH—N), 7.80, 7.72 (s in each case, 1H in each case, N—CH), 4.18 (t, 3 J=7.1 Hz, 2H, N—CH$_2$—), 3.86 (s, 3H, N—CH$_3$), 3.71 (t, $^3$ J=6.6 Hz, 2H, S—O—CH$_2$), 3.71 (p, 3 J=7.3 Hz, 2H, N—CH$_2$—CH$_2$—), 1.47 (k. B., 2H, N—CH$_2$—CH$_2$—CH$_2$—), 1.22 (mult., 12H, S—O—CH$_2$—(CH$_2$)$_6$—), 0.81-0.90 (je tr, je 3H, —CH$_3$) ppm.

13C-NMR (75 MHz, d $^6$-DMSO): δ=136.9, 123.9, 122.6, 66.0, 55.2, 48.8, 36.0, 31.8, 31.6, 29.4, 29.1, 25.9, 22.4, 19.1, 14.2, 13.5 ppm.

Viscosity: η(20° C.)=711 cP

EXAMPLE 3

1-n-Butyl-3-methylimidazolium lauryl sulfate ((BMIM) (C$_{12}$H$_{25}$SO$_4$))

Synthesis:

15.30 g (87.6 mmole) of 1-n-butyl-3-methylimidazolium chloride (BMIM Cl) and 26.60 g (minimum 87.6 mmole) of sodium lauryl sulfate (technical grade, content 95-99%) are dissolved in 50 ml of hot water. The water is slowly removed under vacuum. The solid formed is filtered off after adding methylene chloride to the batch. The filtrate is washed with water until the aqueous phase is colourless and free from chloride. The organic phase is dried over Na$_2$SO$_4$. Concentrating and drying under a high vacuum gives 33.40 g of product (82.5 mmole; 94% of the theoretical yield, based on BMIM Cl) which is obtained as a white beige waxy solid.

Melting point: 44-45° C.

$^1$H-NMR (300 MHz, CD$_3$CN): δ=8.76 (s, 1H, N—CH—N), 7.43, 7.40 (two s, 1H in each case, N—CH$_3$), 4.17 (t, J=7.3 Hz, 2H, N—CH$_2$), 3.87 (s, 3H, N—CH$_3$), 3.83 (t, J=6.6 Hz, 2H, S—O—CH$_2$—), 1.84 (mult., 2H, N—CH$_2$—CH$_2$—), 1.58 (mult., 2H, S—O—CH$_2$—CH$_2$—), 1.40-1.25 (mult., 20H, S—O—CH$_2$—CH$_2$—(CH$_2$)$_9$—; N—CH$_2$—CH$_2$—CH$_2$—), 1.00-0.85 (t, je 3H, —CH$_3$) ppm.

$^{13}$C-NMR (75 MHz, CD3CN): δ=136.2, 123.3, 121.9, 65.9, 48.9-48.7, 35.4, 31.3, 29.1-28.7, 25.5, 22.1, 18.6, 13.1, 12.4 ppm.

Hydrolysis tests were conducted as described below.

EXAMPLE 4

Hydrolysis test with 1-n-butyl-3-methylimidazolium octyl sulfate ((BMIM) (C$_8$H$_{17}$SO$_4$))

Synthesis:

To 5 g of the ionic liquid of 1-n-butyl-3-methylimidazoliumoctyl sulfate ((BMIM) (C$_8$H$_{17}$SO$_4$)), 5 ml of water are added and heated to 80° C. At intervals of 10 min, samples are taken from the reaction solution and pH measurements are carried out. The reaction solution is still pH-neutral after 2 h at 80° C. which suggests that no hydrolytic decomposition of the ionic liquid takes place under these reaction conditions.

COMPARATIVE EXAMPLE 1

Hydrolysis test with 1-n-butyl-3-methylimidazolium methyl sulfate ((BMIM) ($CH_3SO_4$))

Synthesis:
To 5 g of the ionic liquid of 1-n-butyl-3-methylimidazolium methyl sulfate ((BMIM) ($CH_3SO_4$)), 5 ml of water are added and heated to 80° C. At intervals of 10 min, samples are taken from the reaction solution and pH measurements are carried out. The reaction solution exhibits a rapid decrease in the pH to 1-2 after the first measurement. This suggests that, under these reaction conditions, a hydrolytic decomposition of the ionic liquid takes place. Methanol and the acidic hydrogen sulfate anion are liberated during this process.

COMPARATIVE EXAMPLE 2

Hydrolysis test with 1-ethyl-3-methylimidazolium ethyl sulfate ((EMIM) ($C_2H_5SO_4$))

Synthesis:
To 5 g of the ionic liquid of 1-ethyl-3-methylimidazoliumethyl sulfate ((EMIM) ($C_2H_5SO_4$)), 5 ml of water are added and heated to 80° C. At intervals of 10 min, samples are taken from the reaction solution and pH measurements are carried out. The reaction solution exhibits a rapid decrease in the pH to 1-2 after the first measurement. This suggests that, under these reaction conditions, a hydrolytic decomposition of the ionic liquid takes place. Ethanol and the acidic hydrogen sulfate anion are liberated during this process.

EXAMPLE 5

1,3-dialkyl-(2- or 4-hydroxyalkyl)imidazolium alkyl sulfate

Synthesis:
Substantially equimolar amounts of 1,3-dialkyl-4-hydroxyalkylimidazolium halide (or 1,3-dialkyl-2-hydroxyalkylimidazolium halide) and sodium alkyl sulfate are dissolved in water and optionally heated. The water is slowly removed under vacuum. Water immiscible organic solvent, such as methylene chloride, is added to the milieu. Any solid formed is filtered off. The filtrate is washed with water until the aqueous phase is colourless and substantially free from halide. The organic phase is dried over $Na_2SO_4$. Concentrating and drying under a high vacuum yields the product.

EXAMPLE 6

1-alkyl-(2-, 3- or 4-hydroxyalkyl)pyridinium alkyl sulfate

Synthesis:
Substantially equimolar amounts of 1-alkyl-4-hydroxyalkylpyridinium halide (or 1-alkyl-2-hydroxyalkylpyridinium halide or 1-alkyl-3-hydroxyalkylpyridinium halide) and sodium alkyl sulfate are dissolved in water and optionally heated. The water is slowly removed under vacuum. Water immiscible organic solvent, such as methylene chloride, is added to the milieu. Any solid formed is filtered off. The filtrate is washed with water until the aqueous phase is colourless and substantially free from halide. The organic phase is dried over $Na_2SO_4$. Concentrating and drying under a high vacuum yields the product.

EXAMPLE 7

1-alkyl-(2- or 4-hydroxyalkyl)triazolium alkyl sulfate

Synthesis:
Substantially equimolar amounts of 1-alkyl-4-hydroxyalkyltriazolium halide (or 1-alkyl-2-hydroxyalkyltriazolium halide) and sodium alkyl sulfate are dissolved in water and optionally heated. The water is slowly removed under vacuum. Water immiscible organic solvent, such as methylene chloride, is added to the milieu. Any solid formed is filtered off. The filtrate is washed with water until the aqueous phase is colourless and substantially free from halide. The organic phase is dried over $Na_2SO_4$. Concentrating and drying under a high vacuum yields the product.

EXAMPLE 8

1,2-dialkyl-(3- or 4-hydroxyalkyl)pyrazolium alkyl sulfate

Synthesis:
Substantially equimolar amounts of 1,3-dialkyl-4-hydroxyalkylpyrazolium halide (or 1,3-dialkyl-3-hydroxyalkylpyrazolium halide) and sodium alkyl sulfate are dissolved in water and optionally heated. The water is slowly removed under vacuum. Water immiscible organic solvent, such as methylene chloride, is added to the milieu. Any solid formed is filtered off. The filtrate is washed with water until the aqueous phase is colourless and substantially free from halide. The organic phase is dried over $Na_2SO_4$. Concentrating and drying under a high vacuum yields the product.

The disclosures of the references cited herein are hereby incorporated in their entirety.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except by the appended claims. All of the embodiments disclosed and claimed herein can be made and executed without undue experimentation in light of the present disclosure.

What is claimed is:
1. An ionic liquid of the Formula 1,

(cation)(R'$SO_4$)   Formula 1 wherein:
R' is selected from the group consisting of a linear or branched, saturated or unsaturated, aliphatic or alicyclic, functionalized or non-functionalized alkyl radical with 3-36 carbon atoms, wherein R' is optionally functionalized with one or more X groups;
X is selected from the group consisting of an —OH, —OR", —COOH, —COOR", —$NH_2$, —$SO_4$, —F, —Cl, —Br, —I or —CN; and
R" is selected from the group consisting of a branched or linear hydrocarbon chain with 1-12 carbon atoms;
the compound has a melting point of less than 100° C.; and the cation is a nitrogen-containing cation selected from the group consisting of imidazolium cation, pyridinium cation, pyrazolium cation, and triazolium cation;
excluding N-methylpyridinium dodecyl sulfate and N-phenylethylpyridinium dodecyl sulfate.

2. The ionic liquid of claim 1, wherein the cation is selected from the group consisting of:
   a) imidazolium cation with the general formula

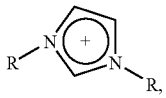

in which the imidazole core is optionally substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group;
   b) pyridinium cation with the general formula

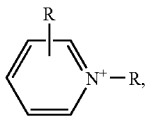

in which the pyridine core is optionally substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group;
   c) pyrazolium cation with the general formula

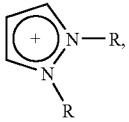

in which the pyrazole core is optionally substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group; and
   d) triazolium cation with the general formula

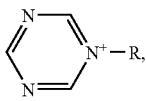

in which the triazole core is optionally substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group; wherein
   e) the radicals $R_1$, $R_2$, $R_3$ are selected independently at each occurrence from the group consisting of:
      i) hydrogen;
      ii) linear or branched, saturated or unsaturated, aliphatic or alicyclic alkyl groups with 1 to 20 carbon atoms;
      iii) heteroaryl groups, heteroaryl-$C_1$-$C_6$ alkyl groups with 3 to 8 carbon atoms in the heteroaryl radical and at least one heteroatom selected from N, O and S which is optionally substituted with at least one group selected from $C_1$-$C_6$ alkyl groups and/or halogen atoms;
      iv) aryl, aryl-$C_1$-$C_6$ alkyl groups with 5 to 12 carbon atoms in the aryl radical, which is optionally substituted with at least one $C_1$-$C_6$ alkyl group and/or a halogen atom; and
   f) the radical R is selected from the group consisting of:
      i) linear or branched, saturated or unsaturated, aliphatic or alicyclic alkyl groups with 1 to 20 carbon atoms;
      ii) heteroaryl-$C_1$-$C_6$ alkyl groups with 3 to 8 carbon atoms in the aryl radical and at least one heteroatom selected from N, O and S, which is optionally substituted with at least one $C_1$-$C_6$ alkyl group and/or halogen atom; and
      iii) aryl-$C_1$-$C_6$ alkyl groups with 5 to 12 carbon atoms in the aryl radical, which is optionally substituted with at least one $C_1$-$C_6$ alkyl group and/or halogen atom.

3. The ionic liquid of claim 2, wherein the anion has an empirical formula selected from the group consisting of $C_4H_9SO_4$, $C_8H_{17}SO_4$ or $C_{12}H_{25}SO_4$.

4. The ionic liquid of claim 2, wherein the compound of the Formula 1 has a melting point of less than 100° C.

5. The ionic liquid of claim 2, wherein the compound of the Formula 1 has a melting point of less than 75° C.

6. The ionic liquid of claim 2, wherein the compound of the Formula 1 has a melting point of less than 50° C.

7. The ionic liquid of claim 2, wherein (R'$SO_4$) is an alkyl sulfate ester, wherein the alkyl moiety is selected from the group consisting of butyl, octyl, 2-ethylhexyl, and dodecyl.

8. The ionic liquid of claim 7, wherein the cation is a nitrogen containing cation selected from the group consisting of 1-ethyl-3-methylimidazolium, 1-butyl-3-methylimidazolium butyl, 1-hexyl-3-methylimidazolium, 1-octyl-3-methylimidazolium, 1-decyl-3-methylimidazolium, 1-dodecyl-3-methylimidazolium, 1-butyl-pyridinium, and trihexyltetradecylphosphonium.

9. The ionic liquid of claim 2, wherein the cation is a nitrogen containing cation selected from the group consisting of 1-ethyl-3-methylimidazolium, 1-butyl-3-methylimidazolium butyl, 1-hexyl-3-methylimidazolium, 1-octyl-3-methylimidazolium, 1-decyl-3-methylimidazolium, 1-dodecyl-3-methylimidazolium, 1-butyl-pyridinium, and trihexyltetradecylphosphonium.

10. The ionic liquid of claim 2, wherein the compound of the Formula 1 is substantially hydrolytically stable in a substantially neutral aqueous solution up to 80° C.

11. The ionic liquid of claim 2, wherein the compound of the Formula 1 has a melting point of less than 25° C.

12. An ionic liquid selected from the group consisting of:
   a) 1-ethyl-3-methylimidazolium butyl sulfate;
   b) 1-ethyl-3-methylimidazolium octyl sulfate;
   c) 1-ethyl-3-methylimidazolium 2-ethylhexyl sulfate;
   d) 1-ethyl-3-methylimidazolium dodecyl sulfate;
   e) 1-butyl-3-methylimidazolium butyl sulfate;
   f) 1-butyl-3-methylimidazolium octyl sulfate;
   g) 1-butyl-3-methylimidazolium 2-ethylhexyl sulfate;
   h) 1-butyl-3-methylimidazolium dodecyl sulfate;
   i) 1-hexyl-3-methylimidazolium butyl sulfate;
   j) 1-hexyl-3-methylimidazolium octyl sulfate;
   k) 1-hexyl-3-methylimidazolium 2-ethylhexyl sulfate;
   l) 1-hexyl-3-methylimidazolium dodecyl sulfate;
   m) 1-octyl-3-methylimidazolium butyl sulfate;
   n) 1-octyl-3-methylimidazolium octyl sulfate;
   o) 1-octyl-3-methylimidazolium 2-ethylhexyl sulfate;
   p) 1-octyl-3-methylimidazolium dodecyl sulfate;
   q) 1-decyl-3-methylimidazolium butyl sulfate;

r) 1-decyl-3-methylimidazolium octyl sulfate;
s) 1-decyl-3-methylimidazolium 2-ethylhexyl sulfate;
t) 1-decyl-3-methylimidazolium dodecyl sulfate;
u) 1-dodecyl-3-methylimidazolium butyl sulfate;
v) 1-dodecyl-3-methylimidazolium octyl sulfate;
w) 1-dodecyl-3-methylimidazolium 2-ethylhexyl sulfate;
x) 1-dodecyl-3-methylimidazolium dodecyl sulfate;
y) 1-butyl-pyridinium butyl sulfate;
z) 1-butyl-pyridinium octyl sulfate;
aa) 1-butyl-pyridinium 2-ethylhexyl sulfate;
bb) 1-butyl-pyridinium dodecyl sulfate;
cc) trihexyltetradecylphosphonium butyl sulfate;
dd) trihexyltetradecylphosphonium octyl sulfate;
ee) trihexyltetradecylphosphonium 2-ethylhexyl sulfate;
ff) trihexyltetradecylphosphonium dodecyl sulfate;
gg) 1,3-dialkyl-(2- or 4-hydroxyalkyl)imidazolium alkyl sulfate;
hh) 1-alkyl-(2-, 3-, or 4-hydroxyalkyl)pyridinium alkyl sulfate;
ii) 1,2-dialkyl-(3- or 4-hydroxyalkyl)pyrazolium alkyl sulfate;
jj) 1-alkyl-(2- or 4-hydroxyalkyl)triazolium alkyl sulfate.

\* \* \* \* \*